United States Patent
Nagatsuka

(10) Patent No.: US 12,417,523 B2
(45) Date of Patent: Sep. 16, 2025

(54) DYNAMIC IMAGING QUALITY CONTROL DEVICE, STORAGE MEDIUM FOR DYNAMIC IMAGING QUALITY CONTROL PROGRAM, AND DYNAMIC IMAGING QUALITY CONTROL METHOD

(71) Applicant: Konica Minolta, Inc., Tokyo (JP)

(72) Inventor: Sumiya Nagatsuka, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 568 days.

(21) Appl. No.: 17/835,194

(22) Filed: Jun. 8, 2022

(65) Prior Publication Data
US 2022/0398713 A1 Dec. 15, 2022

(30) Foreign Application Priority Data
Jun. 15, 2021 (JP) ................. 2021-099252

(51) Int. Cl.
*G06T 7/00* (2017.01)
*A61B 6/00* (2006.01)
(52) U.S. Cl.
CPC .......... *G06T 7/0002* (2013.01); *A61B 6/5205* (2013.01); *A61B 6/542* (2013.01); *G06T 2207/10116* (2013.01); *G06T 2207/30168* (2013.01)
(58) Field of Classification Search
CPC .............. A61B 6/5206; A61B 6/542; G06T 2207/10116; G06T 2207/301168
USPC ........................................... 382/131
See application file for complete search history.

(56) References Cited

U.S. PATENT DOCUMENTS

| | | | | |
|---|---|---|---|---|
| 7,221,735 | B2* | 5/2007 | Inoue | H05G 1/44 378/97 |
| 10,935,617 | B2* | 3/2021 | Keupp | G01R 33/5601 |
| 2021/0404974 | A1* | 12/2021 | Nagatsuka | A61B 6/463 |

FOREIGN PATENT DOCUMENTS

| | | |
|---|---|---|
| JP | 2008-283531 A | 11/2008 |
| JP | 2012-110399 A | 6/2012 |
| JP | 2020-054689 A | 4/2020 |

* cited by examiner

*Primary Examiner* — Gabriel I Garcia
(74) *Attorney, Agent, or Firm* — LUCAS & MERCANTI, LLP

(57) ABSTRACT

A dynamic imaging quality control device that performs quality control regarding dynamic imaging in which a dynamic state of a subject is captured by sequentially emitting radiation to the subject, the dynamic imaging quality control device including: an obtainer that obtains dynamic image data including multiple pieces of frame image data obtained by the dynamic imaging; and a hardware processor that: generates information on quality control regarding smoothness of a dynamic image based on a movement distance of a predetermined object of the subject in the dynamic image data, and outputs the information on the quality control regarding the smoothness of the dynamic image.

14 Claims, 3 Drawing Sheets

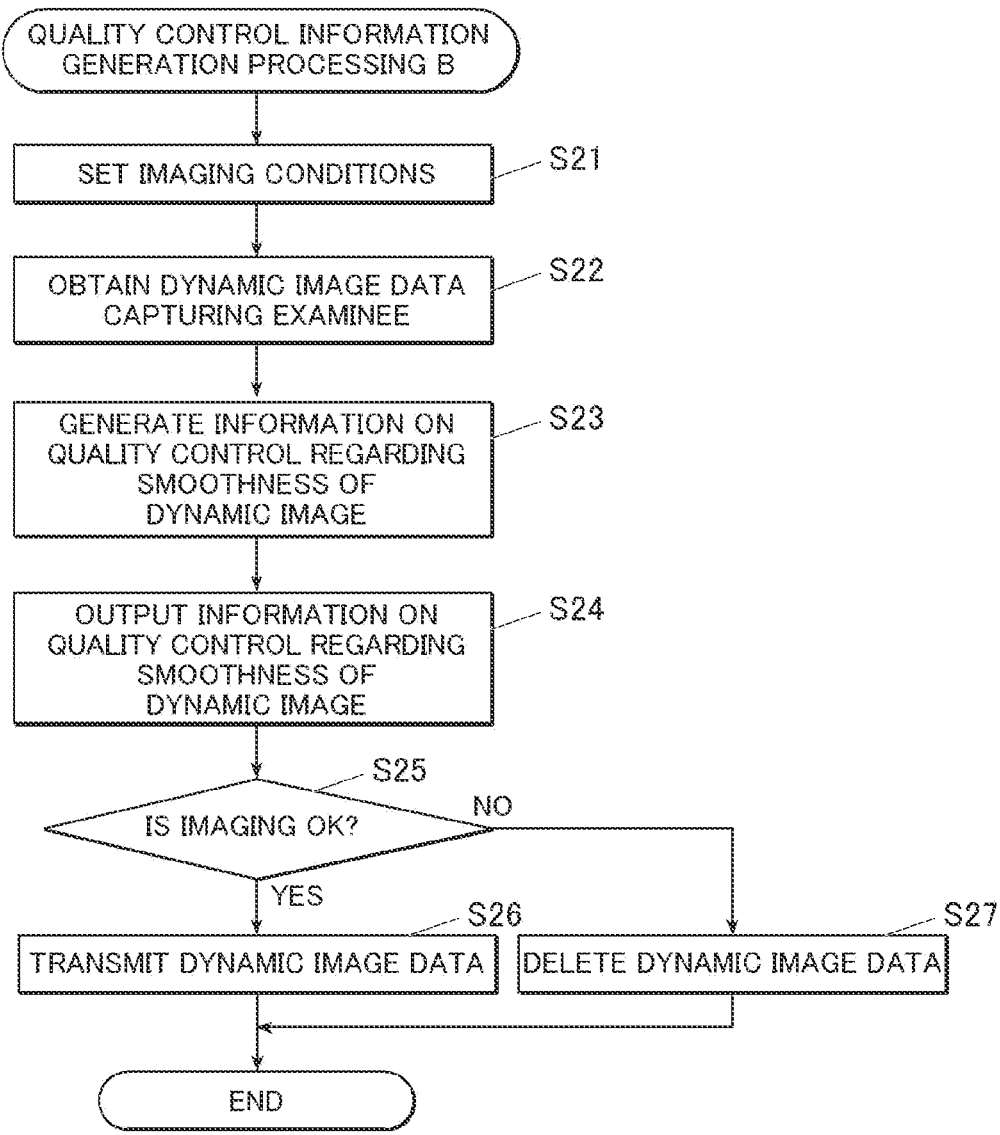

DYNAMIC IMAGING QUALITY CONTROL DEVICE, STORAGE MEDIUM FOR DYNAMIC IMAGING QUALITY CONTROL PROGRAM, AND DYNAMIC IMAGING QUALITY CONTROL METHOD

CROSS-REFERENCE TO RELATED APPLICATIONS

The entire disclosure of Japanese Patent Application No. 2021-099252 filed on Jun. 15, 2021 is incorporated herein by reference in its entirety.

BACKGROUND

Technological Field

The present invention relates to a dynamic imaging quality control device, a storage medium storing a dynamic imaging quality control program, and a dynamic imaging quality control method.

Description of the Related Art

Various techniques have been proposed for carrying out quality control (QC) and quality assurance (QA) of still image radiography.

For example, JP2008-283531A discloses performing QC arithmetic processing for obtaining quality evaluation results with QC image data obtained by radiographing a QC phantom P. Through the processing, the system evaluates evaluation items such as accuracy of displayed dimension, linearity, clarity, and so forth to determine whether the evaluation results of these evaluation items exceed their respective thresholds. On the basis of the determination, the system determines whether the respective evaluation items are "PASS" or "FAIL".

Recently, various devices have been developed for performing dynamic imaging, in which radiation is sequentially emitted to obtain dynamic image data consisting of multiple pieces of frame image data. Like still imaging, it is preferable that dynamic imaging maintain a certain quality level to prevent problems such as misdiagnosis by doctors, increased burdens on radiologists due to reimaging, and reimaging of images that leads to an increase in exposure dose of examinees.

For example, JP2012-110399A states that a frame rate of 3.75 frames/second or higher is desirable for dynamic imaging.

JP2020-54689A describes that the imaging device permits irradiation if the corresponding imaging frame rate contains the number which is N times the irradiation frame rate (e.g., 15, 10, 5) that can be supported by the generation device. The irradiation frame rate is desirably set to a value necessary for the imaging technique. For example, it is stated that an irradiation frame rate of at least 2 Hz is desirable to capture the dynamic state of slow changes such as respiration.

SUMMARY

However, quality control of dynamic imaging, which is rather a new technology in medical fields, has not been fully researched and developed though JP2012-110399A and JP2020-54689A mention it. For example, periodic quality control after the delivery of device is often done manually and individually by radiologists. As the information regarding quality control of dynamic imaging ranges widely as compared with that of still imaging, improvement in the operational efficiency is required.

Dynamic imaging is sometimes used for screening examinations, which are the gateway to medical examinations, because it provides more information than still images and because it is readily available. For this reason, it is sometimes utilized not only in university hospitals but also in clinics where there are no radiographers (specialists in imaging and reading). However, if there is no expert or the expert is inexperienced, he/she may not notice that the quality of the dynamic imaging is not sufficient (e.g., some frame image data is missing, the image is not captured at the appropriate frame rate, or data representing some of the motion in the dynamic image is missing due to them) and the images may be used as is for diagnosis, which may lead to misdiagnosis.

As mentioned above, dynamic imaging has begun to be commercialized in recent years and is likely to spread not only in Japan but also worldwide. In fact, it has been commercialized outside of Japan. In such a situation, compared to still imaging, dynamic imaging needs to continue for tens of seconds to synchronize between the generation device and the imaging device (panel) in order to capture moving images. During dynamic imaging, data loss between the generation device and the imaging device (some frame image data missing) and data transfer loss from the imaging device to the console (some frame image data missing) may occur, and the movement of the examinee's structures (e.g., diaphragm, blood vessels, and motor organs such as bones and joints) in the dynamic image data may appear jerky (not smooth) etc., which may be odd. Then, even if the frame image data quality meets the standard, the quality of dynamic imaging will be degraded due to frame image data leakage.

Similarly, when dynamic imaging is performed with an insufficient frame rate for the motion of the examinee structure, the motion of the examinee structure in the dynamic image data obtained by dynamic imaging appears jerky etc., which may be odd. Even if such dynamic image data is analyzed, it is not possible to obtain analysis results of sufficient quality.

The present invention has been made in consideration of the above matters, and an object of the present invention is to enable proper quality control of smoothness of the dynamic image.

To achieve at least one of the abovementioned objects, according to an aspect of the present invention, a dynamic imaging quality control device reflecting one aspect of the present invention is a dynamic imaging quality control device that performs quality control regarding dynamic imaging in which a dynamic state of a subject is captured by sequentially emitting radiation to the subject, the dynamic imaging quality control device including: an obtainer that obtains dynamic image data including multiple pieces of frame image data obtained by the dynamic imaging; and a hardware processor that: generates information on quality control regarding smoothness of a dynamic image based on a movement distance of a predetermined object of the subject in the dynamic image data, and outputs the information on the quality control regarding the smoothness of the dynamic image.

To achieve at least one of the abovementioned objects, according to another aspect of the present invention, a storage medium for a dynamic imaging quality control program reflecting one aspect of the present invention is storage medium storing a dynamic imaging quality control program for performing quality control regarding dynamic imaging in which a dynamic state of a subject is captured by sequentially emitting radiation to the subject, the dynamic imaging quality control program causing a computer to perform: obtaining that is obtaining dynamic image data including multiple pieces of frame image data obtained by the dynamic imaging; generating that is generating information on quality control regarding smoothness of a dynamic image based on a movement distance of a predetermined object of the subject in the dynamic image data; and outputting that is outputting the information on the quality control regarding the smoothness of the dynamic image.

To achieve at least one of the abovementioned objects, according to another aspect of the present invention, a dynamic imaging quality control method reflecting one aspect of the present invention is A dynamic imaging quality control method for performing quality control regarding dynamic imaging in which a dynamic state of a subject is captured by sequentially emitting radiation to the subject, the dynamic imaging quality control method including: obtaining that is obtaining dynamic image data including multiple pieces of frame image data obtained by the dynamic imaging; generating that is generating information on quality control regarding smoothness of a dynamic image based on a movement distance of a predetermined object of the subject in the dynamic image data; and outputting that is outputting the information on the quality control regarding the smoothness of the dynamic image.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 5 is a flowchart showing the flow of the quality control information generation processing B executed by the controller of FIG. 2 in the second embodiment.

DETAILED DESCRIPTION OF EMBODIMENTS

Hereinafter, embodiments according to the present invention will be described with reference to the drawings. However, the scope of the invention is not limited to the disclosed embodiments or illustrated examples.

First Embodiment

<1. Radiographic Imaging System>

First, the schematic configuration of a radiographic imaging system (hereinafter, system 100) according to a first embodiment of the present invention is described.

The radiographic imaging system is a system capable of performing dynamic imaging, in which the subject is sequentially irradiated with radiation to capture the dynamic state of the subject. Dynamic imaging provides multiple images showing the dynamic state of the subject. The series of images obtained by dynamic imaging is called the dynamic image. Each of the multiple images that make up the dynamic image is called a frame image.

"Dynamic imaging" includes capturing moving images, but does not include taking still images while displaying the moving image. "Dynamic image" includes the moving image, but does not include images obtained by taking still images while displaying the moving image.

Figure 1:
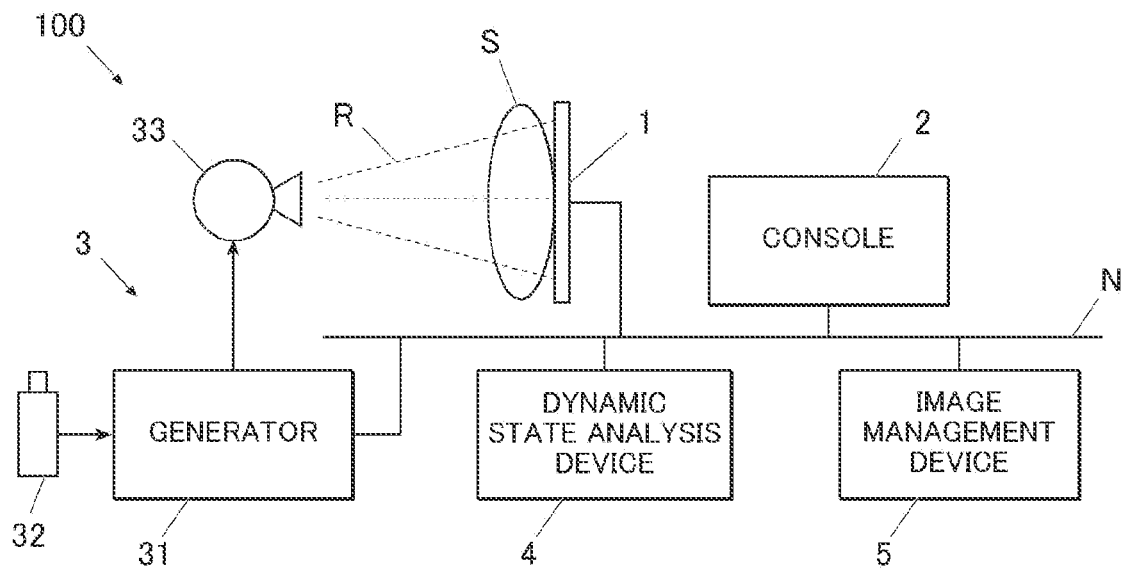
FIG. 1 is a block diagram showing an example of a radiographic imaging system according to embodiments of the present invention.

FIG. 1 is a block diagram showing the system 100.

The system 100 includes a radiographic imaging device (hereinafter, imaging device 1), a console 2, a radiation generation device (hereinafter, generation device 3), a dynamic state analysis device 4, and an image management device 5, as shown in FIG. 1.

The devices 1 to 5 can communicate with each other via a communication network N (e.g., local area network (LAN), wide area network (WAN), the internet), for example.

The system 100 may be installed in a radiography room, or it may be mobile (e.g., in a mobile medical vehicle).

The system 100 may also communicate with a not-illustrated hospital information system (HIS), radiology information system (RIS), etc.

[1-1. Radiation Generation Device]

The generation device 3 includes a generator 31, an irradiation instruction switch 32, and a radiation source 33.

The generator 31 applies a voltage corresponding to preset imaging conditions to the radiation source 33 (tube) in response to the irradiation instruction switch 32 being manipulated.

When the generator 31 applies a voltage to the radiation source 33, the radiation source 33 generates radiation R (e.g., X-rays) with a dose corresponding to the applied voltage.

The generation device 3 in the embodiment generates such radiation R in the manner corresponding to the type of radiographic image (still image or dynamic image) to be generated.

In generating a still image, the generation device 3 emits radiation R only once in response to the irradiation instruction switch 32 being pressed once.

In generating a dynamic image, in response to the irradiation instruction switch 32 being pressed once, the generation device 3 repeats emission of pulse radiation R multiple times per predetermined period of time (e.g., 15 times per second) or continues emission of the radiation R for a predetermined period of time.

In the present invention, "sequentially emit radiation" includes continuous emission in which radiation is continuously emitted, and pulse emission in which radiation is intermittently emitted.

[1-2. Radiographic Imaging Device]

The imaging device 1 generates the digital data of the radiographic image of the imaging site of the subject.

The imaging device 1 in the embodiment is a portable type flat panel detector (FPD).

To be specific, the imaging device 1 in the embodiment includes a sensor substrate, a scanning part, a reading part, a controlling part, and a communication part, etc. which are not illustrated. The sensor substrate includes image capturing elements and switch elements that are arranged two-dimensionally (in a matrix). The image capturing elements generate electric charges corresponding to the dose of the received radiation R. The switch elements accumulate and discharge the electric charges. The scanning part switches on and off each switch element. The reading part reads the amount of electric charges discharged from the respective pixels as signal values. The controlling part controls the parts and generates a radiographic image from the multiple signal values read by the reading part. The communication part transmits data of the generated radiographic image, various signals, and so forth to other devices (console 2, generation device 3, image management device 5, etc.) and receives various kinds of information and signals from the other devices.

The imaging device 1 accumulates/discharges the electric charges and reads signal values in synchronization with the timing of emitting radiation R from the generation device 3. The imaging device 1 thus generates image data of the still image (hereinafter, still image data) or image data of the dynamic image (hereinafter, dynamic image data).

In generating the still image data, the imaging device 1 generates a radiographic image only once in response to the irradiation instruction switch 32 being pressed once.

In generating the dynamic image data, the imaging device 1 generates frame image data constituting the dynamic image data multiple times per a predetermined period of time (e.g., 15 times per second) in response to the irradiation instruction switch 32 being pressed once.

The imaging device 1 transmits the image data generated by the imaging to the console 2.

The imaging device 1 may be integrated with the generation device 3.

[1-3. Console]

The console 2 is an imaging control device that is constituted by a personal computer (PC), a dedicated device or the like, and controls imaging by the imaging device 1 and the generation device 3.

The console 2 sets various imaging conditions (tube voltage, tube current, irradiation time (milliampere-second value), imaging site, imaging direction, frame rate, etc.) in at least either the imaging device 1 or the generation device 3. The console 2 sets the imaging conditions on the basis of examination order information obtained from other system (s) (HIS, RIS, etc.) or according to operation of a user (e.g., radiologist). The examination order information includes, for example, patient information (patient ID, patient name, gender, age, presence or absence of disease, etc.), type of imaging (dynamic/still image), imaging site, imaging direction, department, and type of analysis.

In the embodiment, the console 2 also has a function as a dynamic imaging quality control device of the present invention.

The details of the console 2 will be described later.

[1-4. Dynamic State Analysis Device]

The dynamic state analysis device 4 analyzes the dynamic image data transmitted from the console 2 and transmits the analysis results to the image management device 5 or other devices. The dynamic state analysis device 4 can analyze, for example, ventilation, blood flow, and the amount of movement of a predetermined structure.

[1-5 Image Management Device]

The image management device 5 manages the image data generated by the imaging device 1 and the analysis results generated by the dynamic state analysis device 4.

The image management device 5 includes a Picture Archiving and Communication System (PACS), an image diagnosis workstation (IWS), etc.

<2. Details of Console>

Next, the details of the console 2 will be described.

[2-1. Configuration of Console]

Figure 2:
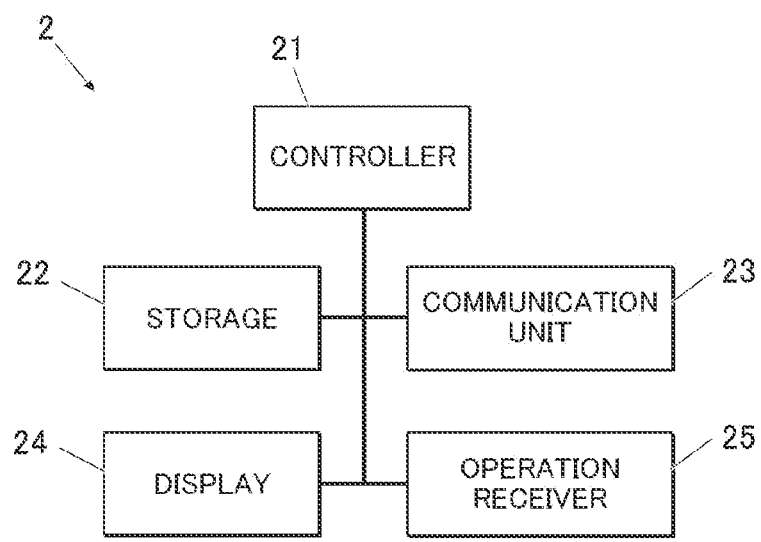
FIG. 2 is a block diagram showing the functional configuration of the console in FIG. 1.

FIG. 2 is a block diagram showing the functional configuration of console 2.

As shown in FIG. 2, the console 2 includes a controller 21 (hardware processor), a storage 22, a communication unit 23, a display 24, and an operation receiver 25. These parts 21-25 are electrically connected via a bus.

The controller 21 includes a central processing unit (CPU) and a random access memory (RAM), a read only memory (ROM), for example.

The ROM stores various programs executed by the CPU, parameters necessary for executing the programs, etc.

The CPU reads various programs stored in the ROM, loads the programs into the RAM, and performs various processes including quality control information generation processing A to be described later in accordance with the loaded programs. The CPU thus centrally controls operations of the components of the console 2.

The controller 21 functions as a generator and an outputter by executing the quality control information generation processing A described later.

The storage 22 includes a nonvolatile memory or a hard disk, etc. and stores various types of data.

The storage 22 stores examination order information transmitted from the RIS, for example.

The communication unit 23 includes a communication module.

The communication unit 23 transmits and receives various kinds of signals and data to and from other devices (e.g., imaging device 1, generation device 3, dynamic state analysis device 4, image management device 5) wirelessly or through wires over the communication network N. The communication unit 23 functions as an obtainer.

The display 24 includes a liquid crystal display (LCD) or a cathode ray tube (CRT), for example. The display 24 displays radiographic images corresponding to image signals received from the controller 21.

The operation receiver 25 includes a keyboard having cursor keys, number keys, and various function keys, a pointing device such as a mouse, and a touchscreen layered on the surface of the display 24. The operation receiver 25 outputs control signals corresponding to the user's operation to the controller 21.

The console 2 may not include the display 24 and the operation receiver 25. For example, the console 2 may receive control signals from an input device separate from the console 2 and output image signals to a display (monitor) separate from the console 2 via the communication unit 23, etc.

When any other device (e.g., image management device 5) includes a display and an operation receiver, the console 2 may receive control signals from the operation receiver of the other device and output image signals to the display of the other device. That is, the display and operation receiver may be shared among the devices.

[2-2. Operation of Console]

Next, the operation of console 2 will be described.

Figure 3:
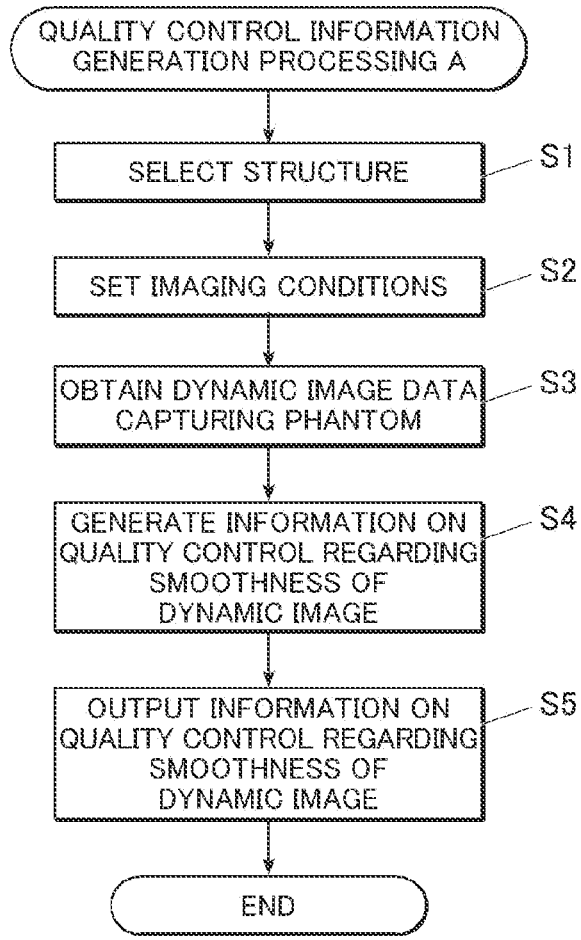
FIG. 3 is a flowchart showing the flow of the quality control information generation processing A executed by the controller of FIG. 2 in the first embodiment.

FIG. 3 is a flowchart showing the flow of quality control information generation processing A executed in the console 2. The quality control information generation processing A is the processing of performing dynamic imaging to a phantom F (see FIG. 4) as the subject S and generating and outputting information (described in detail later) on the quality control regarding the smoothness of the dynamic image on the basis of the obtained dynamic image data. The quality control information generation processing A is the processing that is performed, for example, at the time of factory shipment of the imaging device 1 or generation device 3, at the time of installation in a medical facility, or at the time of quality check of the dynamic images before the start of medical treatment in a medical facility. The quality control information generation processing A is executed by the cooperation of the CPU of controller 21 and the program stored in ROM in response to the user's operation of the instruction to execute quality control information generation processing A by the operation receiver 25.

In the quality control information generation processing A, the controller 21 first allows the user to select the structure to be captured in dynamic imaging for which the information on quality control of the dynamic image is to be generated. (step S1).

For example, the controller 21 displays a list of structures on the display 24 and allows the structure to be selected by the operation receiver 25.

The controller 21 sets the imaging conditions for dynamic imaging to the imaging device 1 and the generation device 3 (step S2).

For example, the controller 21 automatically sets the imaging conditions according to the structure selected in step S1. Alternatively, the imaging conditions may be set by the user's operation of the operation receiver 25. The imaging conditions include radiation irradiation conditions and image reading conditions. Image reading conditions include, for example, pixel size, image size, and frame rate Radiation irradiation conditions include, for example, the tube voltage (kV), tube current (mA), irradiation time (ms), and frame rate of the radiation source. Radiation irradiation conditions may be set by the user directly from the control panel of the generation device 3.

Here, the user positions the phantom F between the radiation source 33 of the generation device 3 and the imaging device 1 and performs positioning.

Figure 4:
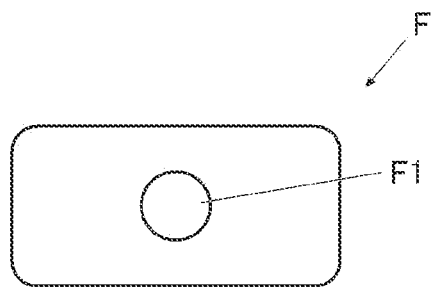
FIG. 4 is a view showing an example of a phantom.

As a phantom F, for example, as shown in FIG. 4, a jig that moves at a speed (mm/s or cm/s) substantially similar to that of the structure selected in step S1 and has a radiation (X-ray) absorbing site F1. For example, when performing quality control of the dynamic image in the case of dynamic imaging of the diaphragm, the user operates the phantom F, which is set to move at a speed substantially similar to that of the diaphragm and a distance substantially similar to that of the diaphragm, by placing it between the radiation source 33 and the imaging device 1. For quality control of the dynamic image in the case of dynamic imaging of the cardiovascular system, the user places and operates a phantom F that is set to move at a speed substantially similar to that of the cardiovascular system and a distance substantially similar to that of the cardiovascular system.

When the user operates the irradiation instruction switch 32, dynamic imaging is initiated.

In other words, the generation device 3 emits radiation R to the phantom F as the subject S.

The imaging device 1 captures the dynamic state of the phantom F at the timing of receiving radiation R from the generation device 3, generates the dynamic image data consisting of multiple pieces of frame image data, and transmits the dynamic image data to the console 2.

When the dynamic image data of the dynamic imaging of phantom F is received (obtained) by the communication unit 23 (step S3), the controller 21 generates the information on the quality control regarding the smoothness of the dynamic image based on the obtained the dynamic image data (step S4).

The information on the quality control regarding the smoothness of the dynamic image is information regarding the smoothness of movement of a predetermined object in the dynamic image data. The predetermined object refers to the radiation absorbing site F1 of the phantom F, which in this embodiment moves according to the structure selected in step S1 (moves at substantially the same speed and over substantially the same distance as the diagnostic object).

For example, the smaller the movement distance (amount of movement) of a structure between adjacent pieces of frame image data in the dynamic image data, the smoother the movement of the structure in the dynamic image data, and the higher the smoothness of the image can be evaluated. However, if the movement distance of the structure between adjacent pieces of frame image data is made too small in an attempt to increase smoothness, the examinee's exposure dose will be unnecessarily high when the irradiation dose for each frame image in dynamic imaging is kept constant, which is undesirable. If the total irradiation dose in dynamic imaging is kept constant, noise in individual frame image data increases, affecting the results of diagnosis and analysis. There are also problems such as the increased data volume of useless dynamic image data, which takes extra time for analysis processing and transfer, and the memory capacity is also overwhelmed by the extra data.

Conversely, if the movement distance of the structure between adjacent pieces of frame image data in the dynamic image data is too large, the movement of the structure in the dynamic image data loses smoothness, resulting in an image that is jerky, odd, and less smooth. When the dynamic state analysis is performed, information is missing and accurate analysis results cannot be obtained.

Therefore, in the embodiment, the controller 21 recognizes the region of the predetermined object from each frame image data of the dynamic image data, that is, the region of the radiation absorbing site F1 of the phantom F that moves according to the structure selected in step S1, and generates the information on the quality control regarding the smoothness of the dynamic image on the basis of the movement distance d of the predetermined object in the dynamic image data captured, e.g., the movement distance d of the predetermined object between predetermined pieces of frame image data in the captured dynamic image data. The "between predetermined pieces of frame image data" preferably includes "between two neighboring (adjacent) pieces of frame image data". This allows for a more accurate evaluation of smoothness than targeting non-adjacent frame image data. However, the target may be between non-adjacent pieces of frame image data. The movement distance d may be calculated from a single piece of frame image data in the dynamic image data. In the dynamic image data, the signal of structures in the previous frame image data (called the previous frame image data) may appear in one frame image data like noise components (afterimage). The length of this noise component (the distance between the signal of the predetermined object in the frame image data and the signal of the predetermined object in the previous frame image data that appeared in the frame image data) is correlated with the movement distance d of the predetermined objects the movement distance d. Therefore, the movement distance d may be calculated based on the length of the noise component.

The information on the quality control regarding the smoothness of the dynamic image includes at least one of the index value related to the smoothness of the dynamic image data (movement distance d, movement distance d/frame rate f, movement speed, acceleration, etc.) and whether or not the index value is within an appropriate range.

For example, the controller 21 calculates the movement distance d of the predetermined object between adjacent pieces of frame image data in the dynamic image data and generates the movement distance d as the information on the quality control regarding the smoothness of the dynamic image. Or, the information indicating whether or not the movement distance d above is within the appropriate range A<d<B is generated as the information on the quality control regarding the smoothness of the dynamic image, where A and B are predetermined constants for each predetermined object in the dynamic image data, and are experimentally determined values.

For example, if the predetermined object is the radiation absorbing site F1 of phantom F that moves according to the diaphragm, A=3 cm and B=10 cm.

For example, if the predetermined object is the radiation absorbing site F1 of phantom F that moves according to the cardiovascular system, A=1 cm and B=5 cm.

For example, if the predetermined object is the radiation absorbing site F1 of phantom F that moves according to the knee joint, A=5 cm and B=15 cm.

The movement distance d may be calculated for each adjacent frame image data, or it may be a representative value (average, maximum, minimum, median, etc.) of the movement distances calculated for respective adjacent frame image data. If the movement distance d is calculated for each adjacent frame image data, for example, the user can easily recognize if there is any missing frame image data.

For example, the controller 21 may calculate the movement distance d per second of the predetermined object in the dynamic image data (i.e., if the frame rate in dynamic imaging is f, the movement distance d to the f-th frame image data), and generate d/f as the information on the quality control regarding the smoothness of the dynamic image. For example, the value d/f, which is the movement distance d per second divided by the frame rate f, can be the information on the quality control regarding the smoothness of the dynamic image, since it represents how far the predetermined object moves when a single frame image is taken.

Alternatively, the information indicating whether the above the movement distance d/f is in the appropriate range A'<d/f<B' may be generated as the information on the quality control regarding the smoothness of the dynamic image, where A' and B' are predetermined constants for each predetermined object in the dynamic image data, and are experimentally determined values.

For example, if the predetermined object is the radiation absorbing site F1 of phantom F, which moves according to the chest, A'=2, B'=4.

For example, if the predetermined object is the radiation absorbing site F1 of the phantom F that moves according to the locomotive organ, A'=0.5 and B'=1.

The frame rate f used to calculate d/f may be the frame rate set as imaging conditions or calculated from the dynamic image data. If the frame rate is calculated from the dynamic image data, in the case of missing some of frame image data due to equipment malfunction or other reasons, this missing can be reflected in the information on the quality control regarding the smoothness of the dynamic image. As a method for calculating the frame rate from the dynamic image data, for example, the time interval (difference in generation time) between the frame mage data and the frame image data directly before or after the frame image data can be calculated for multiple (preferably all) pieces of frame image data of the dynamic image data, and the reciprocal of the calculated value can be used as the frame rate.

The controller 21 may calculate the movement speed and movement acceleration of the predetermined object, based on the calculated the movement distance d, as the information on the quality control regarding the smoothness of the dynamic image. The controller 21 may also generate the information indicating whether the movement speed and/or movement acceleration are within the appropriate range as the information on the quality control regarding the smoothness of the dynamic image.

When the generation of the information on the quality control regarding the smoothness of the dynamic image is finished, the controller 21 outputs the generated information on the quality control regarding the smoothness of the dynamic image (step S5), and ends the quality control information generation processing A.

In step S5, the controller 21 displays at least one or more of the movement distance d, d/f, movement speed, and movement acceleration calculated as the information on the quality control regarding the smoothness of the dynamic image, for example, on the display 24. The dynamic image data obtained in step S3 may also be displayed together.

The inspector at the factory shipment or radiographer knows the approximate appropriate range of the movement distance d, d/f, etc. as described above. By outputting these information as the information on the quality control regarding the smoothness of the dynamic image, the inspector at the factory shipment or radiographer can check whether the smoothness of the dynamic image is appropriate or not, and can properly control the quality of the smoothness of the dynamic image.

For example, the controller 21 may display on the display 24 the information indicating whether the movement distance d or d/f calculated as the information on the quality control regarding the smoothness of the dynamic image is within the appropriate range. This allows even unskilled factory inspectors and radiographers to check whether the smoothness of the dynamic image is appropriate or not, and to properly control the quality of the smoothness of the dynamic image.

Second Embodiment

Next, the second embodiment of the present invention will be described.

The first embodiment has been described for a case of generating and outputting the information on the quality control regarding the smoothness of the dynamic image on the basis of the dynamic image data obtained by dynamic imaging of the phantom F. The second embodiment will be described for a case of generating and outputting the information on the quality control regarding the smoothness of the dynamic image on the basis of the dynamic image data obtained by dynamic imaging of the examinee in the actual examination.

The configuration of the system and device in the second embodiment is the same as that described in the first embodiment, so the description of the first embodiment will be applied, and the operation of console 2 in the second embodiment will be described below.

In the second embodiment, the console 2 executes the quality control information generation processing B shown in FIG. 5. The quality control information generation processing B is executed by the cooperation of the CPU of controller 21 and the program stored in ROM in response to the selection of examination order information for the dynamic imaging by the operation receiver 25 from the examination list screen displayed on the display 24, for example.

First, the controller 21 sets the imaging conditions for dynamic imaging to the imaging device 1 and the generation device 3 (step S21).

For example, on the basis of imaging site, imaging direction, department, etc. included in the examination order information, the controller 21 automatically sets the imaging conditions (image reading conditions, for example, pixel size, image size, frame rate, etc.) to the imaging device 1 and sets the imaging conditions (radiation irradiation conditions, for example, tube voltage (kV), tube current (mA), irradiation time (ms), frame rate, etc. of the radiation source) to the generation device 3. Alternatively, the image reading conditions for the imaging to be performed may be set to the imaging device 1 according to the user's operation of the operation receiver 25. The radiation irradiation conditions may also be set by the user on the operation panel of the generation device 3.

Here, the user positions the subject S (examinee) between the radiation source 33 of the generation device 3 and the imaging device 1 and performs positioning.

When the user operates the irradiation instruction switch 32, dynamic imaging is initiated.

In other words, the generation device 3 emits radiation R to the imaging site of the subject S.

The imaging device 1 captures the dynamic state of the subject S at the timing of receiving radiation R from the generation device 3, generates the dynamic image data consisting of multiple pieces of frame image data, and transmits the dynamic image data to the console 2.

When the dynamic image data capturing the examinee as the subject S is received (obtained) by the communication unit 23 (step S22), the controller 21 generates the information on the quality control regarding the smoothness of the dynamic image based on the obtained dynamic image data (step S23).

As described in the first embodiment, the information on the quality control regarding the smoothness of the dynamic image is information regarding the smoothness of movement of a predetermined object in the dynamic image data. In the second embodiment, the predetermined object refers to the structure of the examinee (subject S). The structure can be specified, for example, based on the examination order information. For example, the correspondence between imaging site (e.g., chest, neck, knee joint, elbow joint, . . . ) and department (e.g., respiratory, cardiology, orthopedics, . . . ) and structure can be stored in the storage 22, and the structure can be specified from the imaging site and department in the examination order information.

The process in step S23 is similar to that described in step S4 of FIG. 3, except that the predetermined object to be recognized from the dynamic image data is the examinee's structure, and thus the same explanation will be applied.

For constants A and B in the appropriate range A<d<B, for example, if the predetermined object is the diaphragm, A=3 cm and B=10 cm. For example, if the predetermined object is a cardiovascular, A=1 cm, B=5 cm. For example, if the predetermined object is the knee joint, A=5 cm and B=15 cm.

For the constants A' and B' in the appropriate range A'<d/f<B', for example, if the predetermined object is the chest, A'=2 and B'=4. For example, if the predetermined object is the locomotive organ, A'=0.5 and B'=1.

When the generation of the information on the quality control regarding the smoothness of the dynamic image is finished, the controller 21 outputs the generated information on the quality control regarding the smoothness of the dynamic image (step S24).

Though the process of step S24 is similar to that of step S5 in FIG. 3, the captured dynamic image data may be displayed on the display 24 together with the information on the quality control regarding the smoothness of the dynamic image. This allows the user (radiographer) to check whether the smoothness of the dynamic image is appropriate by looking at the information on the quality control regarding the smoothness of the dynamic image and the captured dynamic image data.

The user refers to the displayed information on the quality control regarding smoothness, the dynamic image, etc., to determine whether an image suitable for diagnosis has been obtained (imaging is OK) or whether reimaging is required (imaging is NG). The user then operates the operation receiver 25 to input the determination results.

When the determination result indicating imaging is OK is input by the predetermined operation of the operation receiver 25 (step S25; YES), the controller 21 accompanies each of a series of frame image data obtained by dynamic imaging with an identification ID for identifying the dynamic image data, patient information, examination information (information on imaging site, direction of imaging, radiation irradiation conditions, image reading conditions, number indicating the order of imaging (frame number), department, type of analysis, etc.) (e.g., write it in the header area of the image data in DICOM format), and transmits it to the dynamic state analysis device 4 via the communication unit 23 (step S26). If the type of analysis is not specified, the controller 21 may transmit the dynamic image data to the image management device 5. The controller 21 then ends the quality control information generation processing B.

On the other hand, if the determination result indicating imaging is NG is input by the predetermined operation of the operation receiver 25 (step S25; NO), the controller 21 deletes the series of frame image data stored in the storage 22 (step S27) and ends the quality control information generation processing B. In this case, reimaging is necessary. The radiographer performs reimaging by changing imaging conditions such as frame rate, doing maintenance on the imaging device 1 or the generation device 3, or using another imaging device 1 or the generation device 3. In other words, quality control of the smoothness of the dynamic image can be properly performed.

In the case where the information on whether the index value such as the movement distance d or d/f is within the appropriate range or not is generated as the information on the quality control regarding the smoothness of the dynamic image, when the index value is not within the appropriate range, the controller 21 may prompt reimaging by displaying on the display 24 (or outputting by voice) notification information such as "The smoothness of the dynamic image is not appropriate. Please perform imaging again." If the index value is not within the appropriate range, the controller 21 controls the dynamic image data not having appropriate smoothness not to be sent to the dynamic state analysis device 4 or the image management device 5 (prohibits the transmission of dynamic image data not having appropriate smoothness to the dynamic state analysis device 4 or the image management device 5), for example, by preventing the user from inputting that imaging is OK. This prevents providing, for analysis and diagnosis, the dynamic image data which does not have appropriate smoothness of the dynamic image.

When the dynamic state analysis device 4 receives the dynamic image data from the console 2, it performs analysis processing according to the type of analysis accompanying the dynamic image data and transmits the analysis results to the image management device 5, so as to be associated with the dynamic image data and its accompanying information.

The image management device 5 stores and manages the received dynamic image data and analysis result so as to be associated with the accompanying information.

In such a way, in the second embodiment, the information on the quality control regarding the smoothness of the dynamic image in the dynamic image data which was obtained by actually performing the dynamic imaging to the examinee in the examination is generated and output. Thus, the user such as the radiographer can appropriately perform the quality control of the smoothness of the dynamic image.

The controller 21 may obtain the dynamic image data by pre-imaging before the main imaging of dynamic imaging for the imaging site of the examinee in the examination, and generate the information on the quality control regarding the smoothness of the dynamic image on the basis of the obtained dynamic image data.

MODIFICATION EXAMPLE

In the second embodiment, it is explained that the console 2 has the function of the dynamic imaging quality control device of the present invention and generates and outputs the information on the quality control regarding the smoothness of the dynamic image from the dynamic image data obtained by dynamic imaging. However, the dynamic state analysis device 4 and the image management device 5 may function as the dynamic imaging quality control device of the present invention and generate and output the information on the quality control regarding the smoothness of the dynamic image from the received the dynamic image data.

For example, the controller of the dynamic state analysis device 4 performs a process similar to step S23 of FIG. 5 prior to performing the analysis on the dynamic image data. If the information on the quality control regarding the smoothness of the dynamic image indicates that the smoothness of the dynamic image is not appropriate, then the controller performs control to display (or output audibly) notification information such as "The dynamic image cannot be used for analysis because its smoothness is not appropriate." Or, if the information on the quality control regarding the smoothness of the dynamic image generated based on the dynamic image data indicates that the smoothness of the dynamic image is not appropriate, the controller of the dynamic state analysis device 4 may control not to perform the analysis process using the dynamic image data. This prevents incorrect analysis results from being provided for diagnosis.

In addition, for example, the controller of the image management device 5 performs a process similar to step S23 of FIG. 5 on the received dynamic image data, and stores the generated information on the quality control regarding the smoothness of the dynamic image so as to be associated with the dynamic image data. When the controller receives a request from a client terminal to display the dynamic image data, the controller performs control to display (or output audibly) notification information to the client terminal, such as "The requested dynamic image data cannot be used for diagnosis because its smoothness is not appropriate." Alternatively, if the information on the quality control regarding the smoothness of the dynamic image generated based on the dynamic image data requested by the client terminal indicates that the smoothness of the dynamic image is not appropriate, the controller of the image management device 5 may control not to display the dynamic image data to the client terminal. This prevents the dynamic image data that does not have the appropriate smoothness from being provided for diagnosis.

Though the first embodiment, second embodiment and modification example thereof according to the present invention have been described above, the present invention is not limited to the above embodiments or modification example. Modifications can be appropriately made within the scope of the present invention.

For example, in the above embodiments, information on the quality control of the smoothness of the dynamic image is output by the display 24, but it may also be output by an audio output device or may be output by the communication unit 23 to an external device.

Moreover, for example, the above description discloses an example of using a hard disk, a semiconductor nonvolatile memory, etc. as a computer readable medium of the program according to the present invention, but the medium is not limited to this example. As other computer readable medium, portable recording media such as CD-ROM can be applied. Carrier wave is also applicable as a medium to provide the data of the program according to the present invention via communication lines.

Although embodiments of the present invention have been described and illustrated in detail, the disclosed embodiments are made for purposes of illustration and example only and not limitation. The scope of the present invention should be interpreted by terms of the appended claims.

What is claimed is:

1. A dynamic imaging quality control device that performs quality control regarding dynamic imaging in which a dynamic state of a subject is captured by sequentially emitting radiation to the subject, the dynamic imaging quality control device comprising:
    an obtainer that obtains dynamic image data including multiple pieces of frame image data obtained by the dynamic imaging; and
    a hardware processor that:
        generates information on quality control regarding smoothness of a dynamic image based on a movement distance of a predetermined object of the subject in the dynamic image data, wherein the hardware processor generates the information on quality control by calculating a movement distance of the predetermined object between adjacent pieces of frame image data of the dynamic image and determining an appropriate range for the predetermined object from a plurality of different ranges for respective objects, and
        outputs the information on the quality control regarding the smoothness of the dynamic image by indicating whether the movement distance is within the appropriate range.

2. The dynamic imaging quality control device according to claim 1, wherein
    the subject is a phantom, and
    the predetermined object is an X-ray absorbing site in the phantom.

3. The dynamic imaging quality control device according to claim 1, wherein
the subject is an examinee, and
the predetermined object is a structure in the examinee.

4. The dynamic imaging quality control device according to claim 3, wherein the hardware processor generates the information on the quality control regarding the smoothness of the dynamic image from dynamic image data obtained by pre-imaging before main imaging in the dynamic imaging of the examinee.

5. The dynamic imaging quality control device according to claim 1, wherein, when the movement distance is d and the predetermined range is A<d<B, the A and the B are constants determined by the predetermined object.

6. The dynamic imaging quality control device according to claim 1, wherein the hardware processor generates the information on the quality control regarding the smoothness of the dynamic image based on the movement distance and a value of a frame rate in the dynamic imaging of the subject.

7. The dynamic imaging quality control device according to claim 6, wherein the hardware processor generates the information on the quality control regarding the smoothness of the dynamic image based on whether an evaluation value based on the movement distance and the value of the frame rate is within a second predetermined range.

8. The dynamic imaging quality control device according to claim 7, wherein when the movement distance is d, the frame rate is f and the second predetermined range is A'<d/f<B', the A' and the B' are constants determined by the predetermined object.

9. A non-transitory computer-readable storage medium storing a dynamic imaging quality control program for performing quality control regarding dynamic imaging in which a dynamic state of a subject is captured by sequentially emitting radiation to the subject, the dynamic imaging quality control program causing a computer to perform:
obtaining that is obtaining dynamic image data including multiple pieces of frame image data obtained by the dynamic imaging;
generating that is generating information on quality control regarding smoothness of a dynamic image based on a movement distance of a predetermined object of the subject in the dynamic image data, wherein the generating includes calculating a movement distance of the predetermined object between adjacent pieces of frame image data of the dynamic image and determining an appropriate range for the predetermined object from a plurality of different ranges for respective objects; and
outputting that is outputting the information on the quality control regarding the smoothness of the dynamic image by indicating whether the movement distance is within the appropriate range.

10. The storage medium according to claim 9, wherein, in the generating, the information on the quality control regarding the smoothness of the dynamic image is generated based on the movement distance and a value of a frame rate in the dynamic imaging of the subject.

11. The storage medium according to claim 10, wherein, in the generating, the information on the quality control regarding the smoothness of the dynamic image is generated based on whether an evaluation value based on the movement distance and the value of the frame rate is within a second predetermined range.

12. A dynamic imaging quality control method for performing quality control regarding dynamic imaging in which a dynamic state of a subject is captured by sequentially emitting radiation to the subject, the dynamic imaging quality control method comprising:
obtaining that is obtaining dynamic image data including multiple pieces of frame image data obtained by the dynamic imaging;
generating that is generating information on quality control regarding smoothness of a dynamic image based on a movement distance of a predetermined object of the subject in the dynamic image data, wherein the generating includes calculating a movement distance of the predetermined object between adjacent pieces of frame image data of the dynamic image and determining an appropriate range for the predetermined object from a plurality of different ranges for respective objects; and
outputting that is outputting the information on the quality control regarding the smoothness of the dynamic image by indicating whether the movement distance is within the appropriate range.

13. The dynamic imaging quality control method according to claim 12, wherein, in the generating, the information on the quality control regarding the smoothness of the dynamic image is generated based on the movement distance and a value of a frame rate in the dynamic imaging of the subject.

14. The dynamic imaging quality control method according to claim 13, wherein, in the generating, the information on the quality control regarding the smoothness of the dynamic image is generated based on whether an evaluation value based on the movement distance and the value of the frame rate is within a second predetermined range.

* * * * *